(12) United States Patent
Farris (10) Patent No.: US 7,175,622 B2
(45) Date of Patent: Feb. 13, 2007

(54) SPINAL ROD SYSTEM

(75) Inventor: Robert A. Farris, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 11/109,882

(22) Filed: Apr. 19, 2005

(65) Prior Publication Data

US 2005/0277932 A1    Dec. 15, 2005

Related U.S. Application Data

(63) Continuation-in-part of application No. 10/868,073, filed on Jun. 15, 2004.

(51) Int. Cl.
*A61B 17/56* (2006.01)

(52) U.S. Cl. .................................... 606/61

(58) Field of Classification Search ............ 606/60–61, 606/69, 72–73
See application file for complete search history.

(56) References Cited

U.S. PATENT DOCUMENTS

| | | | |
|---|---|---|---|
| 4,361,141 A | | 11/1982 | Tanner |
| 4,771,767 A | * | 9/1988 | Steffee .................. 606/61 |
| 4,773,402 A | * | 9/1988 | Asher et al. .............. 606/61 |
| 4,854,304 A | | 8/1989 | Zielke |
| 5,053,034 A | * | 10/1991 | Olerud .................... 606/61 |
| 5,154,718 A | | 10/1992 | Cozad et al. |
| 5,217,461 A | | 6/1993 | Asher et al. |
| 5,330,472 A | | 7/1994 | Metz-Stavenhagen |
| 5,330,474 A | | 7/1994 | Lin |
| 5,336,223 A | * | 8/1994 | Rogers .................... 606/61 |
| 5,403,314 A | | 4/1995 | Currier |
| 5,425,732 A | | 6/1995 | Ulrich |
| 5,486,174 A | | 1/1996 | Fournet-Fayard et al. |
| 5,487,744 A | * | 1/1996 | Howland .................. 606/61 |
| 5,562,660 A | | 10/1996 | Grob |
| 5,575,790 A | | 11/1996 | Chen et al. |
| 5,593,408 A | | 1/1997 | Gayet et al. |
| 5,630,816 A | | 5/1997 | Kambin |
| 5,643,260 A | * | 7/1997 | Doherty .................. 606/61 |
| 5,658,284 A | * | 8/1997 | Sebastian et al. ........... 606/61 |
| 5,993,449 A | * | 11/1999 | Schlapfer et al. .......... 606/60 |
| 6,099,528 A | | 8/2000 | Saurat |
| 6,102,912 A | | 8/2000 | Cazin et al. |
| 6,106,527 A | | 8/2000 | Wu et al. |
| 6,171,311 B1 | * | 1/2001 | Richelsoph .............. 606/61 |
| 6,241,730 B1 | | 6/2001 | Alby |
| 6,328,739 B1 | * | 12/2001 | Liu et al. ................. 606/61 |
| 6,328,741 B1 | | 12/2001 | Richelsoph |

(Continued)

FOREIGN PATENT DOCUMENTS

EP    0 612 507 A1    2/1994
EP    0 584 803 A1    3/1994

*Primary Examiner*—Eduardo C. Robert
*Assistant Examiner*—Annette Reimers
(74) *Attorney, Agent, or Firm*—Krieg DeVault LLP (57) ABSTRACT

A spinal rod system includes a first rod and a second rod engaged to one another in end-to-end fashion. A coupling mechanism allows the spinal rod system to be assembled with rod portions having the desired characteristics while minimizing the footprint of the coupling arrangement between the first and second rods.

23 Claims, 9 Drawing Sheets

U.S. PATENT DOCUMENTS

| | | |
|---|---|---|
| 6,520,962 B1 * | 2/2003 | Taylor et al. .................. 606/61 |
| 6,676,661 B1 * | 1/2004 | Martin Benlloch et al. ... 606/61 |
| 6,685,705 B1 * | 2/2004 | Taylor ......................... 606/61 |
| 2004/0220575 A1 * | 11/2004 | Biedermann et al. ......... 606/73 |
| 2005/0154388 A1 * | 7/2005 | Roussouly et al. ........... 606/61 |
| 2005/0171537 A1 * | 8/2005 | Mazel et al. .................. 606/61 |
| 2005/0228376 A1 * | 10/2005 | Boomer et al. ................ 606/61 |
| 2005/0228378 A1 * | 10/2005 | Kalfas et al. .................. 606/61 |

* cited by examiner

SPINAL ROD SYSTEM

CROSS-REFERENCE TO RELATED APPLICATION

This application is a continuation-in-part of U.S. patent application Ser. No. 10/868,073, filed on Jun. 15, 2004, which incorporated herein by reference in its entirety.

BACKGROUND

The spine is subject to various pathologies that compromise its load bearing and support capabilities. Such pathologies of the spine include, for example, degenerative diseases, the effects of tumors and, of course, fractures and dislocations attributable to physical trauma. In the treatment of diseases, malformations or injuries affecting spinal motion segments (which include two or more adjacent vertebrae and the disc tissue or disc space therebetween), and especially those affecting disc tissue, it has long been known to remove some or all of a degenerated, ruptured or otherwise failing disc. It is also known that artificial discs, fusion implants, or other interbody devices can be placed into the disc space after disc material removal. External stabilization of spinal segments alone or in combination with interbody devices also provides advantages. Elongated rigid plates, rods and other external stabilization devices have been helpful in the stabilization and fixation of a spinal motion segment, in correcting abnormal curvatures and alignments of the spinal column, and for treatment of other conditions.

While external rod systems have been employed along the vertebrae, the geometric and dimensional features of these rod systems and patient anatomy constrain the surgeon during surgery and prevent optimal placement and attachment along the spinal column. For example, elongated, one-piece rods can be difficult to maneuver into position along the spinal column, and also provide the surgeon with only limited options in sizing and selection of the rod system to be placed during surgery.

SUMMARY

In one aspect, a rod system having a first rod attachable to a second rod in end-to-end fashion allows the surgeon to select from rods having various dimensions and/or other characteristics to construct a rod system that is optimal for pre-operative planning and to address conditions encountered during surgery. The end-to-end attachment minimizes the intrusiveness of the rod system into the anatomy adjacent the connection location.

In another aspect, a rod system includes a first rod attachable to a second rod in end-to-end fashion with a coupling mechanism that axially and torsionally constrains the first and second rods to one another. In one form, the end-to-end attachment arrangement is aligned along a common axis of the rods. In another form, the axes of the rods are offset laterally relative to one another.

In a further aspect, a rod system includes a first rod attachable to a second rod in end-to-end fashion with a coupling mechanism. In one form, the coupling mechanism includes a coupling body on one rod that axially receives a coupling member on the other rod and engagement of the coupling member with the coupling body axially constrains the first and second rods to one another. In another embodiment, the coupling mechanism includes a coupling body that axially receives and constrains each of the first and second rods. The coupling body can be configured to assemble the rods in axial alignment or with their axes laterally offset from one another.

In another aspect, a method for assembling a spinal rod system includes: providing a first spinal rod with a first rod portion for attachment to the spinal column, said first rod portion including a first characteristic and a coupling member at an end of the rod portion; providing a second spinal rod with a second rod portion for attachment to the spinal column, said second rod portion including a second characteristic and a coupling body at an end of the rod portion; and axially constraining the first spinal rod to the second spinal rod with the coupling member engaging the coupling body and the first and second spinal rods centered along a longitudinal axis of the spinal rod system.

In another aspect, a method for assembling a spinal rod system includes providing a first spinal rod with a first rod portion for attachment to the spinal column, said first rod portion including a first characteristic and a coupling member at an end of the rod portion extending along an axis of the first spinal rod; providing a second spinal rod with a second rod portion for attachment to the spinal column, said second rod portion including a second characteristic; threadingly engaging the coupling member of the first rod to a coupling body extending between the first and second rods; and threadingly engaging an engaging member to the coupling body in contact with the coupling member of the first rod to torsionally constrain the first rod in the coupling body with the first spinal rod and the second spinal rod in end-to-end arrangement relative to one another.

These and other aspects will be apparent from the description that follows.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is hereby intended. Any such alterations and further modifications in the illustrated devices, and any such further applications of the principles of the invention as illustrated herein being contemplated as would normally occur to one skilled in the art to which the invention relates.

Figure 1:
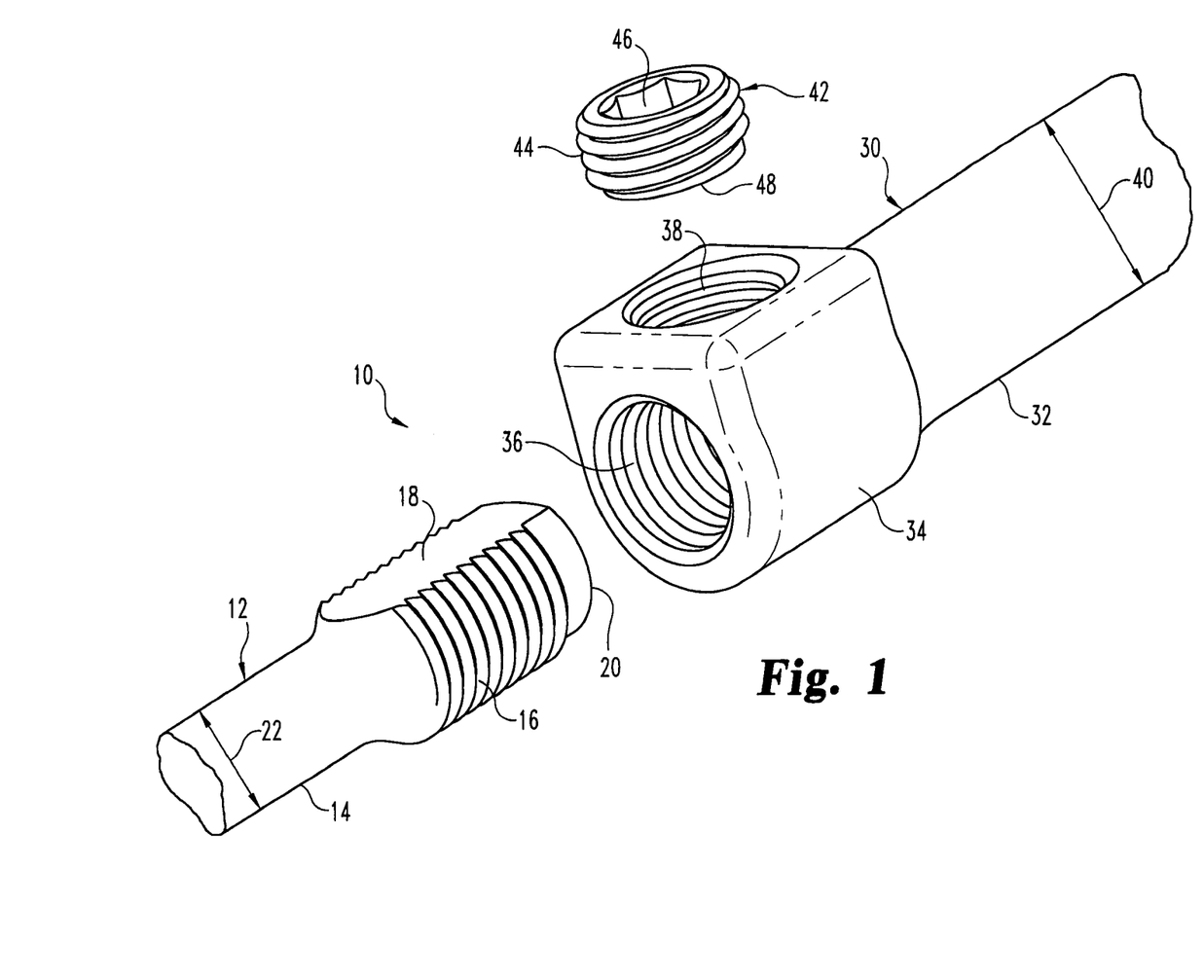
FIG. 1 is an exploded perspective view of a portion of one embodiment rod system.

In FIG. 1 there is shown a spinal rod system 10 including a first rod 12 and a second rod 30. First rod 12 and second rod 30 are releasably coupled to one another in end-to-end fashion with a coupling mechanism 28. Coupling mechanism 28 includes a coupling body on one of the first and second rods 12, 30 and a coupling member on the other of the first and second rods 12, 30. The coupling mechanism 28 is configured to secure rods 12, 30 to one another in end-to-end fashion. This minimizes the footprint or intrusiveness of the coupling mechanism into the tissue surrounding the rod system, and maximizes the length of the rod portion of each rod available for positioning and/or attachment along the spinal column.

Figure 5:
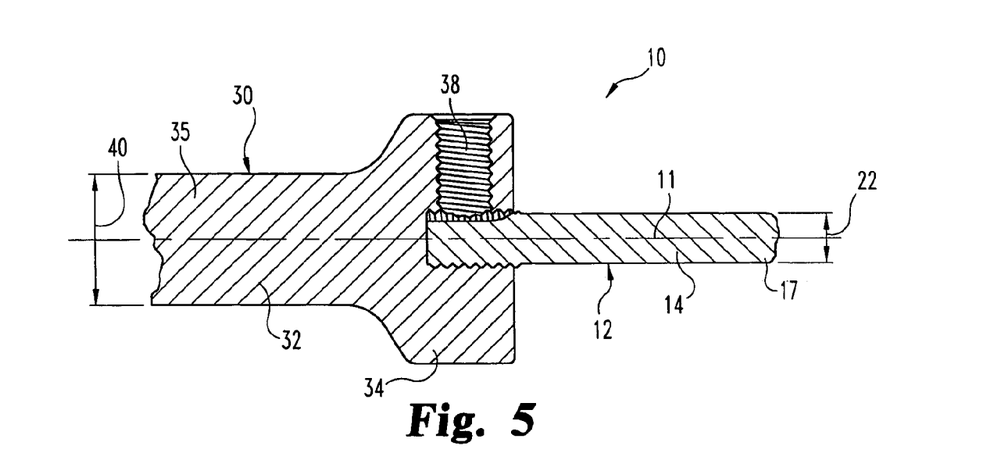
FIG. 5 is a section view of the rod system of FIG. 1 assembled with the engaging member removed from the coupling mechanism.

First rod 12 includes a first rod portion 14 and coupling member 16 at a first end of first rod portion 14. Rod portion 14 extends from coupling member 16 to an opposite second end 17 (FIG. 5.) Second rod 30 includes coupling body 34 at a first end thereof. Rod portion 32 extends from coupling body 34 to an opposite second end 35 (FIG. 5.) One or both of the second ends 17, 35 of rod portions 14, 32 may include a coupling member, a coupling body, or simply provide a terminal end shaped like the corresponding rod portion 14, 32 as shown. In the embodiments illustrated herein, although only one coupling mechanism is shown, one or more of the first and second rods can be adapted for engagement with another rod at each end thereof so that three or more rods may comprise the rod system. The rod portions can be secured to vertebrae of the spinal column system with any one or combination of hooks, screws, bolts, multi-axial screws, staples, cables or wires, sutures, clamps, and/or other attachment devices and systems, with or without interbody fusion devices or implants between vertebrae.

The first rod portion can be provided with a characteristic that differs from a characteristic of the second rod portion. The coupling mechanism allows rods of differing characteristics and rods having the same characteristics to be secured to one another in end-to-end fashion to provide a rod system that is adapted for the anatomy, surgical condition, or surgical procedure. In one embodiment, the characteristic includes a cross-sectional dimension of the rod portions. Other embodiments contemplate selection criteria for selection and assembly of the rod portion to include any one or combination of characteristics, including length, contouring, flexibility, surface features, shape, section modulus, elasticity, materials and material properties, and coatings, for example. For example, in one embodiment a first rod provides a rigid support between a first set of anchors, while the second rod is flexible to provide dynamic stabilization between a second set of anchors. The second rod can be in the form of a tether, cable wire, spring, bumper, or other motion permitting construct.

Figure 2:
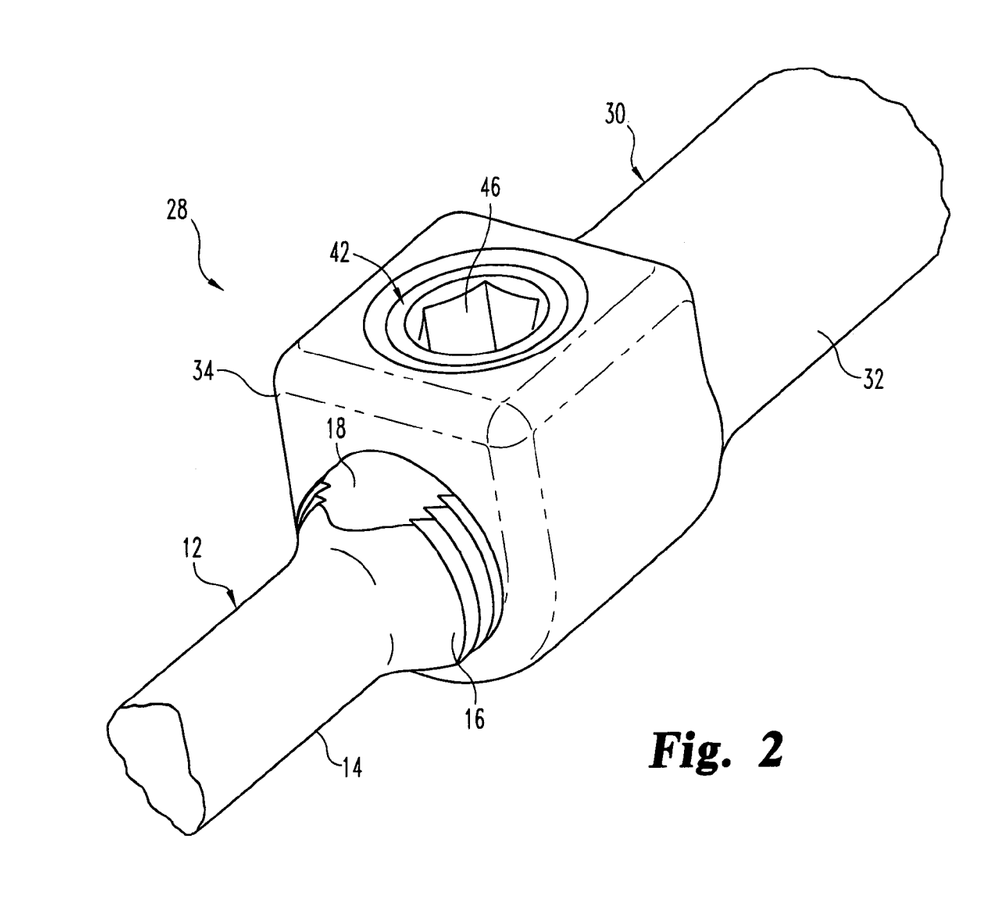
FIG. 2 is a perspective view of the rod system of FIG. 1 assembled.

As shown in FIGS. 1–2 and 5, rod portion 14 extends along longitudinal axis 11 and includes a first cross-sectional dimension 22 between opposite sides thereof transverse to longitudinal axis 11. Similarly, rod portion 32 extends along longitudinal axis 11 and includes a second cross-sectional dimension 40 between opposite sides thereof transverse to longitudinal axis 11. In the illustrated embodiment, cross-sectional dimension 22 corresponds to a diameter of a cylindrical rod portion 14 that is smaller than a diameter corresponding to cross-sectional dimension 40 of a cylindrical rod portion 32. In one specific application, the diameter of first rod portion 14 is sized to extend along a first portion of the spine, such as the cervical region, and the diameter of second rod portion 32 is sized to extend along a second portion of the spine, such as the thoracic region. Other systems contemplate multiple rod portions coupled to one another in end-to-end fashion with characteristics adapted for positioning along any one or combination of the sacral, lumbar, thoracic and cervical regions of the spinal column.

Figure 3:
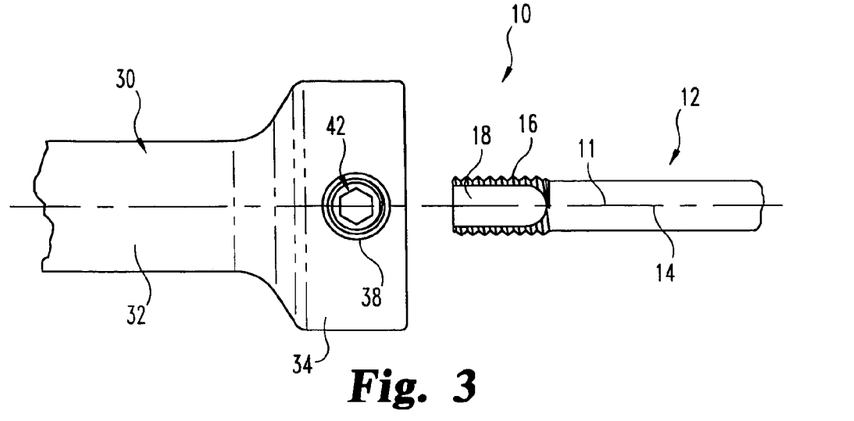
FIG. 3 is an exploded elevational view of the rod system of FIG. 1.
Figure 4:
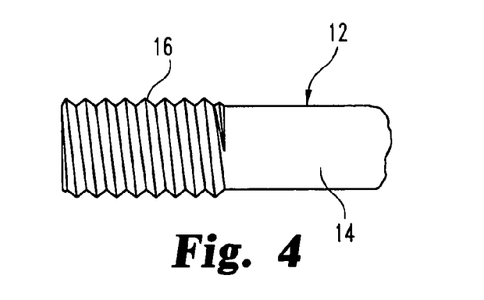
FIG. 4 is a view of a first rod rotated 180 degrees about its longitudinal axis from its FIG. 3 orientation.

Coupling member 16 includes a threaded outer surface extending from rod portion 14 to an end member 20 lacking threads. Coupling member 16 further includes a contact portion 18 along at least one side thereof, as also shown in FIG. 3. Contact portion 18 can be formed by a cutout providing a flat surface extending along coupling member 16. Contact portion 18 can also include a concave surface, a convex surface, a receptacle, or other suitable configuration for contacting an engaging member. As shown in FIG. 5, the thread pattern of coupling member 16 extends completely therearound between the opposite sides of contact portion 18. Other embodiments contemplate that multiple contact portions are provided along coupling member 16 to provide multiple engagement locations for engaging member 42, as discussed further below.

Coupling body 34 can be enlarged relative to rod portion 32 to provide a flange or hub to which coupling member 16 can be releasably engaged. In the illustrated embodiment, coupling body 34 is a cubic block, although other shapes are also contemplated, such as rectangular, cylindrical and non-uniform shapes. Coupling body 34 includes a first bore 36 formed internally therein that extends along and opens along longitudinal axis 11 at an end of coupling body 34. Coupling body 34 further includes a second bore 38 extending therein transversely to first bore 36. As further shown in FIG. 5, second bore 38 can be internally threaded for receipt of an engagement member. Second bore 38 can also be orthogonal to first bore 36, although other orientations are also contemplated.

As shown in FIGS. 2 and 5, rods 12, 30 can be assembled in end-to-end fashion and aligned along longitudinal axis 11 with coupling member 16 received in bore 36 and axially constrained by threaded engagement with coupling body 34. End member 20 facilitates positioning and alignment of coupling member 16 in bore 36, preventing or reducing the possibility of cross-threading coupling member 16 with coupling body 34. The axial load between rods 12, 30 is carried by the engagement between coupling member 16 and coupling body 34, which are also aligned along the axis 11 of rod system 10 when engaged. Accordingly, torsional loading of the components of rod system 10 is minimized since the rods 12, 30 are connected to one another in end-to-end fashion along axis 11. Furthermore, the footprint of coupling mechanism 28 both transversely to rods 12, 30 and along rods 12, 30 is minimized, making the procedure for positioning rod system 10 less invasive, providing additional rod length for contouring and attachment of fasteners for engagement with the spinal column, and minimizing the number of components employed in securing the rods 12, 30 to one another.

Engaging member 42 is positionable in second bore 38 and engageable to coupling member 16 to prevent rod 12 from disengaging from rod 30. In one embodiment, contact portion 18 of coupling member 16 is oriented toward second bore 38, and engaging member 42 is an externally threaded set screw 44 engageable in second bore 38. A tool engaging recess 46 is provided for engagement with a tool, such as a hex driver, to allow the set screw 44 to be driven into second bore 38. Set screw 44 is driven into second bore 38 so that end 48 is in contact with contact portion 18, preventing coupling member 16 from rotating in body 34 and resisting torsional loading between rods 12, 30.

With contact surface 18 aligned with bore 38, the rod portions 14, 32 are oriented in a predetermined alignment with one another determined by the location of contact surface 18 and bore 38 relative to the respective rod portions 14, 32. For example, if one or both of rod portions 14, 32 are provided with non-circular cross-sections, through-holes, or other characteristic along their respective lengths, the characteristics can be oriented relative to contact surface 18 and/or bore 38 so that when contact surface 18 is engaged by engaging member 42, the characteristic of rod portion 14 is positioned in a desired alignment relative rod portion 32. In this manner, the rod portions 14, 32 can be secured with these characteristics in a predetermined alignment relative to one another, and maintained in this alignment by the engagement of engaging member 42 with contact surface 18.

Other embodiments contemplate other arrangements for coupling mechanism 28. For example, engaging member 42 can be a pin that is received in a hole or recess in coupling member 16. Coupling body 34 can be a nut rotatably captured on the end of rod portion 32. Coupling mechanism 28 can include a bayonet locking type device, or a spring-biased ball plunger in coupling member 16 that is received in a detent in coupling body 34.

Figure 6:
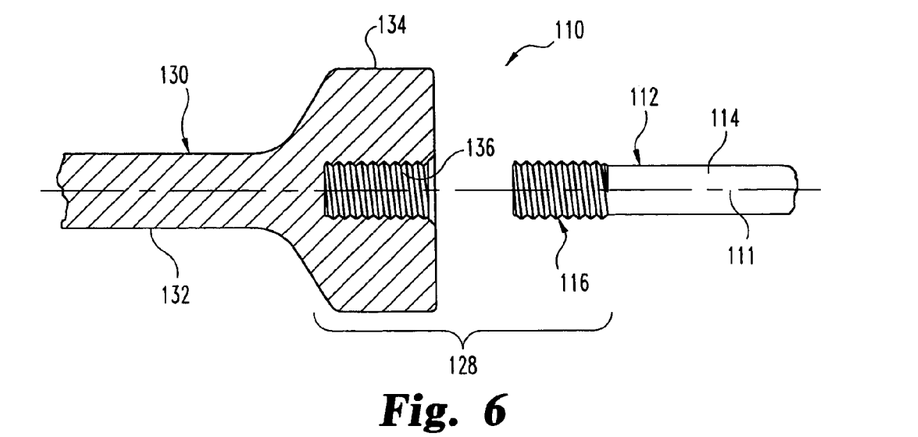
FIG. 6 is an exploded elevation view in partial section of another embodiment rod system

In FIG. 6, there is shown another embodiment rod system 110 extending along a longitudinal axis 111 and including a first rod 112 having rod portion 114 and coupling member 116. A second rod 130 includes rod portion 132 and a coupling body 134 with an axial bore 136. First and second rod portions 114, 132 can be provided with differing characteristics and axially constrained to one another in end-to-end fashion. Body 134 does not include a second bore for an engaging member, and coupling member 116 can be provided completely threaded therearound. To torsionally constrain coupling member 116 in coupling body 134, coupling member 116 can be provided with locking threads to prevent first and second rods 112, 130 from rotating relative to one another. In another embodiment, a simple threaded engagement is provided to axially constrain rods 112, 130 to one another, and relative rotation of rods 112, 130 is resisted by the engagement of rods 112, 130 to the spinal column.

Figure 7:
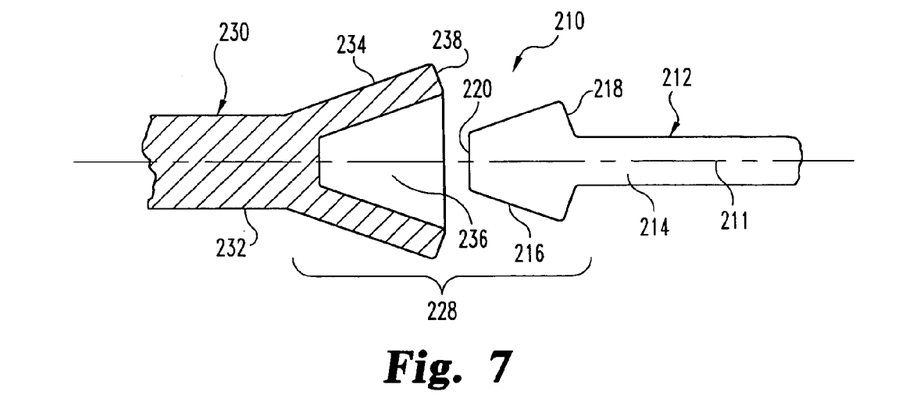
FIG. 7 is an exploded elevation view in partial section of another embodiment rod system.

In FIG. 7, there is shown another embodiment rod system 210 including a first rod 212 and a second rod 230 extending along a longitudinal axis 211. First rod 212 includes a first rod portion 214 and second rod 230 includes a second rod portion 232. First and second rod portions 214, 232 can be provided with differing characteristics and attached to one another in end-to-end fashion with a coupling mechanism 228. First rod 212 includes a coupling member 216 at an end of rod portion 214. Coupling member 216 is externally tapered toward the first end 220 of rod 212, and forms a lip 218 extending about rod portion 214. Coupling body 234 includes an axial bore that is tapered from a first end 238 of second rod 230 toward rod portion 232. Engaging member 216 is press fit into bore 236 so that the tapered outer surface is received in the flared bore to frictionally engage and axially and torsionally constrain first rod 212 to second rod 230 in end-to-end fashion. It is further contemplated that an engaging member can be provided extending between coupling body 234 and coupling member 216 to provide additional fixation in addition to the friction fit between coupling body 234 and coupling member 216.

Figure 8:
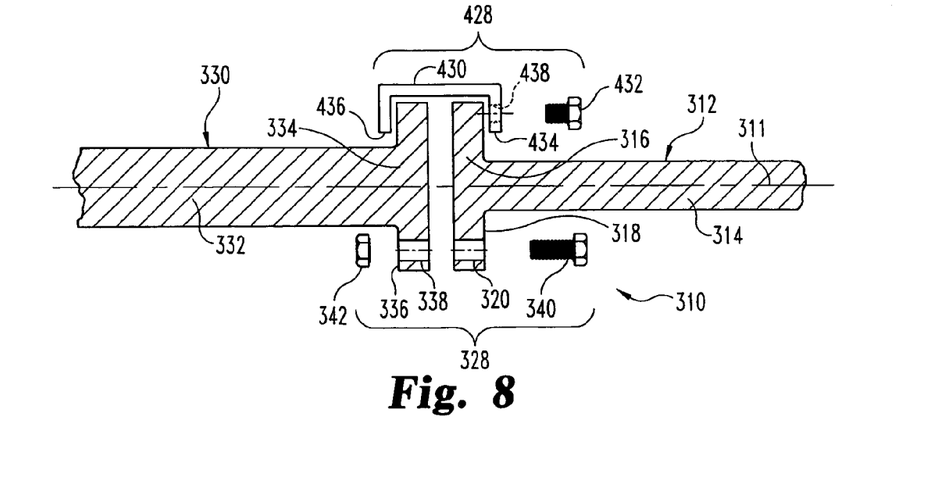
FIG. 8 is an exploded elevation view of another embodiment rod system with two embodiments of a coupling mechanism for coupling the rods to one another.

In FIG. 8, there is shown another embodiment rod system 310 including a first rod 312 and a second rod 330 extending along longitudinal axis 311. First rod 312 includes a first rod portion 314 and second rod 330 includes a second rod portion 332. First rod 312 includes a coupling member at an end of rod portion 314 in the form of a flange or hub 316 extending around first rod portion 314. Flange 316 forms a lip 318 extending about rod portion 314. Second rod 330 includes a coupling body at an end thereof that is also in the form of a flange or hub 334. Flange 334 extends around and forms a lip 336 about second rod portion 332. Flanges 316, 334 are positionable in abutting engagement with one another in end-to-end fashion so that rods 312, 330 having differing characteristics can be secured to one another to provide rod system 310.

Coupling mechanism 328 includes a fastener 340 extendable through aligned bores 320, 338 extending parallel to axis 311 through the flanges 316, 334. A nut 342 is engageable with fastener 340 to axially constrain rods 312, 330 together in end-to-end fashion. It is contemplated that a number of fasteners can be positioned about the flanges to provide additional axial constraint and also torsional constraint to rods 312, 330. Although fastener 340 has been shown as a bolt with a nut, other fasteners are also contemplated, including rivets, screws, and bolts threadingly engaged to the flange bores, for example.

Another embodiment coupling mechanism 428 is shown in FIG. 8 that includes a clamping member 430 and an engaging member 432. Clamping member 430 includes arms 434, 436 at opposite ends thereof that extend along adjacent ones of the flanges 316, 334. Fastener 432 extends parallel to axis 311 and is engageable to a bore 438 in arm 434. Fastener 432 is positionable in contact with flange 316 to bias arm 436 into contact with flange 334. Flanges 316, 334 are drawn toward one another to position the flanges in end-to-end contact and axially constrain rods 312, 330 relative to one another. It is contemplated that a number of clamping members can be provided about flanges 316, 334 to provide a secure clamping arrangement to prevent rods 312, 330 from pivoting or splaying relative to one another. It is further contemplated that clamping member 430 can be sized to extend along a portion of the perimeter of flanges 316, 334, and a number of fasteners 432 are provided to clamp first and second rods 312, 330 to one another.

Figure 9:
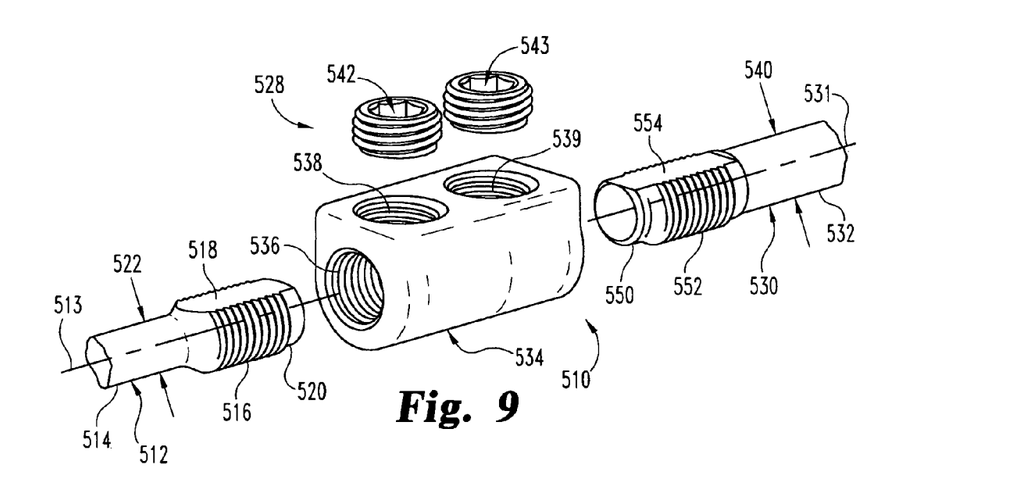
FIG. 9 is an exploded perspective view of a portion of another rod system.
Figure 10:
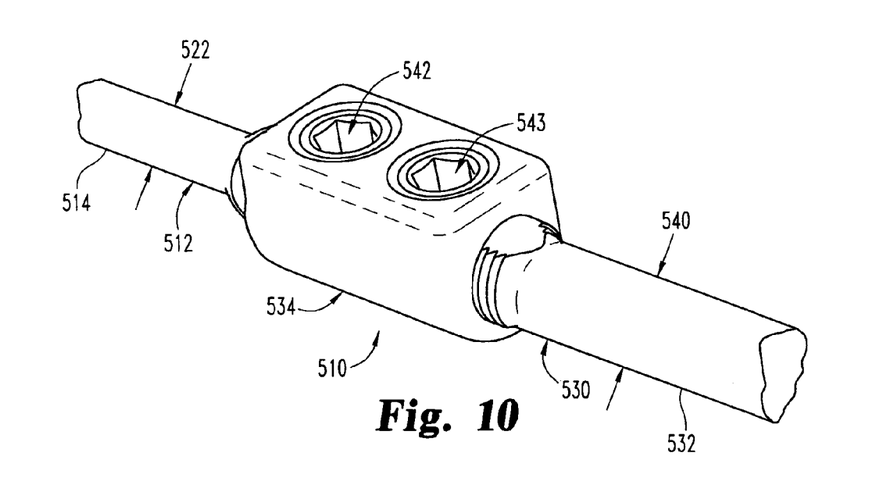
FIG. 10 is an assembled perspective view of the rod system of FIG. 9.

In FIGS. 9–10 there is shown a spinal rod system 510 including a first rod 512 and a second rod 530. First rod 512 and second rod 530 are releasably coupled to one another in end-to-end fashion with a coupling mechanism 528. Coupling mechanism 528 includes a coupling body 534 releasably engageable to each of the first and second rods 512, 530. The coupling mechanism 528 is configured to secure rods 512, 530 to one another in end-to-end fashion while minimizing the footprint or intrusiveness of the coupling mechanism into the tissue surrounding the rod system and maximizing the length of the rod portion of each rod available for positioning and/or attachment along the spinal column.

First rod 512 includes a first rod portion 514 and coupling member 516 at a first end of first rod portion 514. Rod portion 514 extends from coupling member 516 to an opposite second end (not shown.) Second rod 530 includes coupling member 552 at a first end thereof. Rod portion 532 extends from coupling member 516 to an opposite second end (not shown.) One or both of the second ends of rod portions 514, 532 may include a coupling member, a coupling body, or simply provide a terminal end shaped like the corresponding rod portion 514, 532 as shown.

First rod portion 514 can be provided with a characteristic that differs from a characteristic of second rod portion 532. The coupling mechanism 528 allows rods of differing characteristics to be secured to one another in end-to-end fashion to provide a rod system that is adapted for the anatomy, surgical condition, or surgical procedure. In one embodiment, the characteristic includes a cross-sectional dimension of the rod portions 514, 532. Other embodiments contemplate selection criteria for selection and assembly of the rod portion to include any one or combination of characteristics, including length, contouring, flexibility, surface features, shape, section modulus, elasticity, materials and material properties, and coatings, for example.

As shown in FIGS. 9–10, rod portion 514 extends along longitudinal axis 513 and includes a first cross-sectional dimension 522 between opposite sides thereof transverse to longitudinal axis 513. Similarly, rod portion 532 extends along longitudinal axis 531 and includes a second cross-sectional dimension 540 between opposite sides thereof transverse to longitudinal axis 531. In the illustrated embodiment, cross-sectional dimension 522 corresponds to a diameter of a cylindrical rod portion 514 that is smaller than a diameter corresponding to cross-sectional dimension 540 of a cylindrical rod portion 532. In one specific application, the diameter of first rod portion 514 is sized to extend along a first portion of the spine, such as the cervical region, and the diameter of second rod portion 532 is sized to extend along a second portion of the spine, such as the thoracic region. Other systems contemplate multiple rod portions coupled to one another in end-to-end fashion with characteristics adapted for positioning along any one or combination of the sacral, lumbar, thoracic and cervical regions of the spinal column.

Coupling member 516 includes a threaded outer surface extending from rod portion 514 to an end member 520 lacking threads. Coupling member 516 further includes a contact portion 518 along at least one side thereof. Contact portion 518 can be formed by a cutout providing a flat surface extending along coupling member 516. Contact portion 518 can also include a concave surface, a convex surface, a receptacle, or other suitable configuration for contacting an engaging member. The thread pattern of coupling member 516 can extend completely therearound between the opposite sides of contact portion 518. Other embodiments contemplate that multiple contact portions are provided along coupling member 516 to provide multiple engagement locations for engaging member 542, as discussed further below.

Rod 530 similarly includes a coupling member 552 including a threaded outer surface extending from rod portion 532 to an end member 550 lacking threads. Coupling member 552 further includes a contact portion 554 along at least one side thereof. Contact portion 554 can be formed by a cutout providing a flat surface extending along coupling member 552. Contact portion 554 can also include a concave surface, a convex surface, a receptacle, or other suitable configuration for contacting an engaging member. The thread pattern of coupling member 552 can extend completely therearound between the opposite sides of contact portion 554. Other embodiments contemplate that multiple contact portions are provided along coupling member 552 to provide multiple engagement locations for engaging member 543, as discussed further below.

Coupling body 534 can be enlarged relative to rod portions 514, 532 to provide an axial first bore 536 that threadingly receives the respective coupling members 516, 552. In the illustrated embodiment, coupling body 534 is a cubic block, although other shapes are also contemplated, such as rectangular, cylindrical and non-uniform shapes. First bore 536 extends along and opens along longitudinal axes 513, 531 when aligned with the respective rods 512, 530 at opposite ends of coupling body 534. Coupling body 534 further includes a first trans-axial bore 538 and an adjacent second trans-axial bore 539 extending therein transversely to longitudinal axes 513, 531 and in communication with first bore 536. Bores 538, 539 can be internally threaded for receipt of respective ones of the engagement members 542, 543. Bores 538, 539 can be orthogonal to first bore 536, although other orientations are also contemplated.

Rods 512, 530 can be assembled in end-to-end fashion and aligned along longitudinal axes 513, 531 with coupling member 516 received in one end of bore 536 and coupling member 552 received in the opposite end of bore 536. Coupling members 516, 552 are axially constrained by threaded engagement with coupling body 534. End members 520, 550 facilitate positioning and alignment of coupling members 516, 552 in bore 536, preventing or reducing the possibility of cross-threading coupling members 516, 552 with coupling body 534. The axial load between rods 512, 530 is carried by the engagement between coupling members 516, 552 and coupling body 534, which are also aligned along the axes 513, 531 when engaged. Accordingly, torsional loading of the components of rod system 510 is minimized since the rods 512, 530 are connected to one another in end-to-end fashion with axes 513, 531 aligned via coupling mechanism 528. Furthermore, the footprint of coupling mechanism 528 both transversely to rods 512, 530 and along rods 512, 530 is minimized, making the procedure for positioning rod system 510 less invasive, providing additional rod length for contouring and attachment of fasteners for engagement with the spinal column, and minimizing the number of components employed in securing the rods 512, 530 to one another.

Engaging members 542, 543 are positionable in first trans-axial bore 538 and second trans-axial bore 539 and engageable to respective ones of the coupling members 516, 552 to prevent rods 512, 530 from disengaging from coupling body 534. In one embodiment, contact portion 518 of coupling member 516 is oriented toward first trans-axial bore 538, and engaging member 542 is an externally threaded set screw engageable in first trans-axial bore 538. Engaging member 542 is driven into first trans-axial bore 538 so that it is in contact with contact portion 518, preventing coupling member 516 from rotating in coupling body 534 and resisting torsional loading of rod 512. Similarly, contact portion 554 of coupling member 552 is oriented toward second bore 539, and engaging member 543 is an externally threaded set screw engageable in second trans-axial bore 539. Engaging member 542 is driven into bore 539 so that it is in contact with contact portion 554, preventing coupling member 552 from rotating in coupling body 534 and resisting torsional loading of rod 530.

With contact surface 518 aligned with bore 538, the rod portion 514 is oriented in a predetermined alignment determined by the location of contact surface 518 and bore 538 relative to the respective rod portion 514. Similarly, with contact surface 554 aligned with bore 539, the rod portion 532 is oriented in a predetermined alignment determined by the location of contact surface 554 and bore 539 relative to the respective rod portion 532. For example, if one or both of rod portions 514, 532 are provided with non-circular cross-sections, through-holes, or other characteristic along their respective lengths, the characteristics can be oriented relative to contact surface 518, 554 and/or bores 538, 539 so that engagement by the respective engaging members 542, 543 provides a desired alignment. The rod portions 514, 532 can be secured with these characteristics in a predetermined alignment relative to one another, and maintained in this alignment by the engagement of engaging members 542, 543 with contact surfaces 518, 554.

Figure 11:
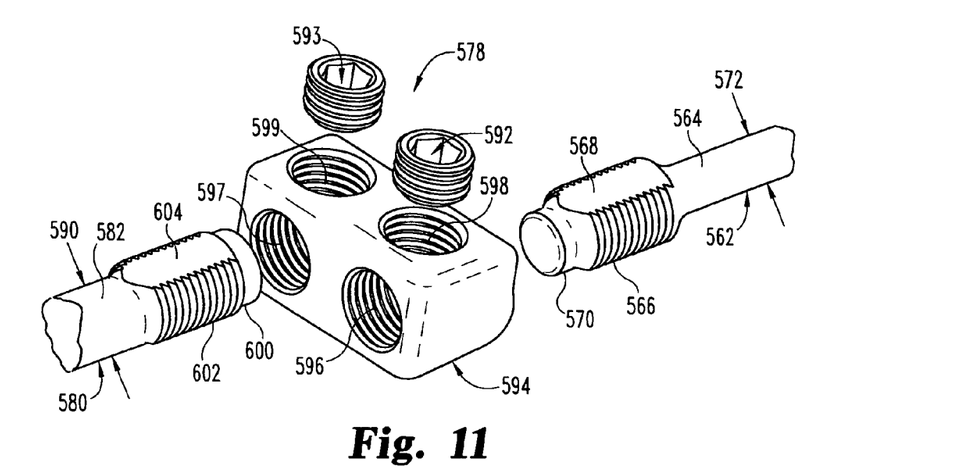
FIG. 11 is an exploded perspective view of a portion of another rod system.
Figure 12:
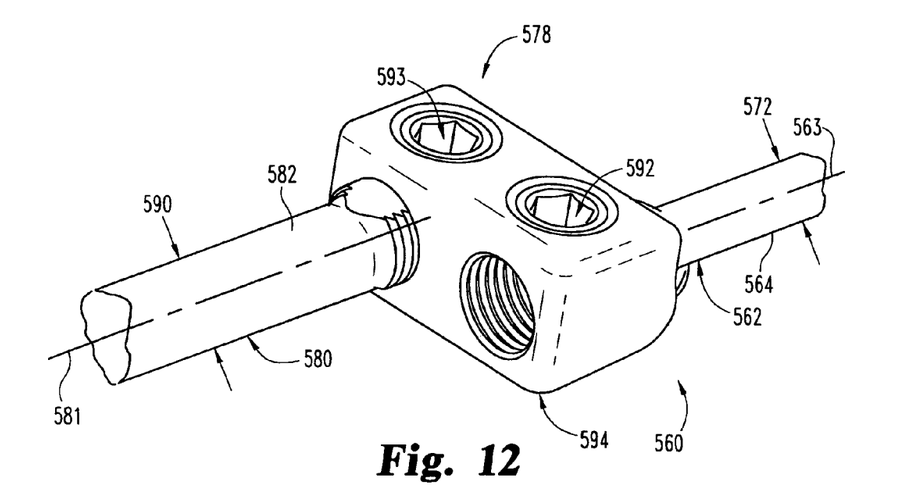
FIG. 12 is an assembled perspective view of the rod system of FIG. 11.

Referring to FIGS. 11 and 12, there is shown another embodiment a spinal rod system 560 including a first rod 562 and a second rod 580. First rod 562 and second rod 580 are releasably coupled to one another in end-to-end fashion with a coupling mechanism 578. Coupling mechanism 578 includes a coupling body 594 releasably engageable to each of the first and second rods 562, 580. The coupling mechanism 578 is configured to secure rods 562, 530 to one another in end-to-end fashion with their longitudinal axes 563, 581 laterally offset from one another. This allows the relative positioning of rods 562, 580 to be offset as may be desirable to accommodate the spinal anatomy while minimizing the footprint or intrusiveness of the coupling mechanism into the tissue surrounding the rod system, and maximizing the length of the rod portion of each rod available for positioning and/or attachment along the spinal column.

Like rods 512, 530 discussed above, first rod 562 includes a first rod portion 564 and coupling member 566 at a first end of first rod portion 564. Rod portion 564 extends from coupling member 566 to an opposite second end (not shown.) Second rod 580 includes coupling member 602 at a first end thereof. Rod portion 582 extends from coupling member 602 to an opposite second end (not shown.) Rod portions 564, 582 can be provided with characteristics that differ from one another.

As shown in FIGS. 11–12, rod portion 564 extends along longitudinal axis 563 and includes a first cross-sectional dimension 572 between opposite sides thereof transverse to longitudinal axis 563. Similarly, rod portion 582 extends along longitudinal axis 581 and includes a second cross-sectional dimension 590 between opposite sides thereof transverse to longitudinal axis 581. In the illustrated embodiment, cross-sectional dimension 572 corresponds to a diameter of a cylindrical rod portion 564 that is smaller than a diameter corresponding to cross-sectional dimension 590 of a cylindrical rod portion 582. In still other embodiments, the diameters of the rod portions 582, 564 are the same.

Coupling member 566 includes a threaded outer surface extending from rod portion 564 to an end member 570 lacking threads. Coupling member 566 further includes a contact portion 568 along at least one side thereof. Contact portion 568 can be formed by a cutout providing a flat surface extending along coupling member 566. Contact portion 568 can also include a concave surface, a convex surface, a receptacle, or other suitable configuration for contacting an engaging member. The thread pattern of coupling member 566 can extend completely therearound between the opposite sides of contact portion 568. Other embodiments contemplate that multiple contact portions are provided along coupling member 566 to provide multiple engagement locations for engaging member 592, as discussed further below.

Rod 580 similarly includes a coupling member 602 including a threaded outer surface extending from rod portion 582 to an end member 600 lacking threads. Coupling member 602 further includes a contact portion 604 along at least one side thereof. Contact portion 604 can be formed by a cutout providing a flat surface extending along coupling member 602. Contact portion 604 can also include a concave surface, a convex surface, a receptacle, or other suitable configuration for contacting an engaging member. The thread pattern of coupling member 602 can extend completely therearound between the opposite sides of contact portion 604. Other embodiments contemplate that multiple contact portions are provided along coupling member 602 to provide multiple engagement locations for engaging member 593, as discussed further below.

Coupling body 594 can be enlarged relative to rod portions 564, 582 to provide an axial first bore 596 that threadingly receives coupling member 566, and an axial second bore 597 offset laterally from and extending parallel to first bore 596 to threadingly receive coupling member 602. In the illustrated embodiment, coupling body 594 is a rectangular block, although other shapes are also contemplated, such as cubic, cylindrical and non-uniform shapes. First bore 596 extends along and opens on longitudinal axis 563 when aligned with rod 562, and second bore 597 extends along and opens on longitudinal axis 581 when aligned with rod 580. Coupling body 594 further includes a first trans-axial bore 598 and an adjacent second trans-axial bore 599 extending therein transversely to respective ones of the longitudinal axes 563, 581 and in communication with respective ones of the bores 596, 597. Bores 598, 599 can be internally threaded for receipt of respective ones of the engagement members 592, 593. Bores 598, 599 can be orthogonal to the respective bores 596, 597, although other orientations are also contemplated.

Rods 562, 580 can be assembled in end-to-end fashion with coupling member 566 received in first bore 596 and coupling member 602 received in second bore 597. Coupling members 566, 602 are axially constrained by threaded engagement with coupling body 594. End members 570, 600 facilitate positioning and alignment of coupling members 566, 602 in bores 596, 597, preventing or reducing the possibility of cross-threading coupling members 566, 602 with coupling body 594. The axial load between rods 562, 580 is carried by the engagement between coupling members 566, 602 and coupling body 594.

The axial restraint provided by the threaded engagement of rods 562, 580 to coupling body 594 allows the length of coupling body 594 along axes 563, 581 to be minimized, thus minimizing its intrusion into the adjacent anatomy and maximizing the rod length available for attachment of connection elements. The lateral offset provided by coupling mechanism 578 allows application of rods 562, 580 in anatomical locations where alignment of axes 563, 581 would not be optimal. Engaging members 592, 593 are positionable in first trans-axial bore 598 and second trans-axial bore 599, respectively, and engageable to respective ones of the coupling members 566, 602 to contact the aligned contact portions 568, 604 to prevent rods 562, 580 from disengaging from coupling body 594.

Figure 13:
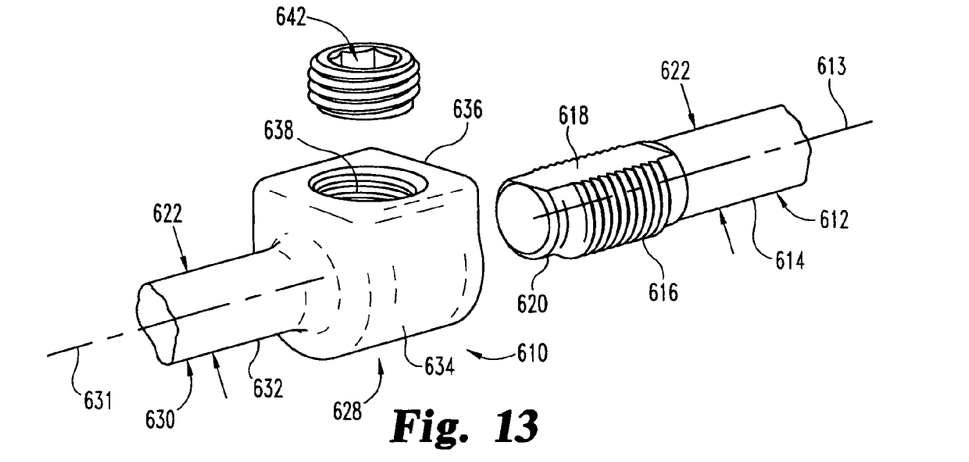
FIG. 13 is an exploded perspective view of a portion of another rod system.
Figure 14:
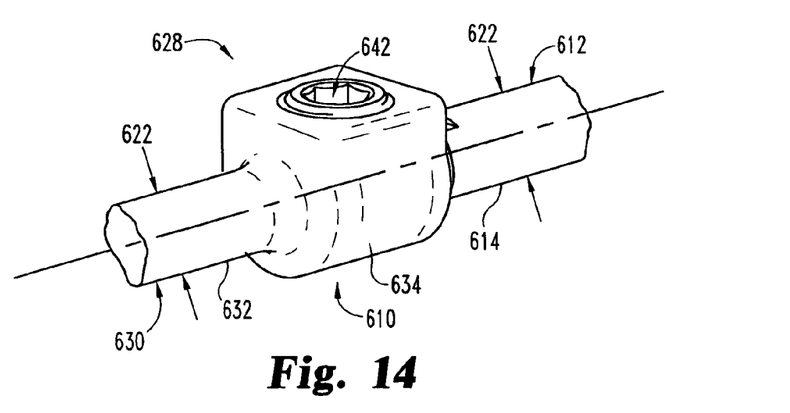
FIG. 14 is an assembled perspective view of the rod system of FIG. 13.

FIGS. 13–14 shown another embodiment connection assembly 610 similar to the embodiment shown in FIGS. 1–2, except for rods 612, 630 having the same cross-sectional dimension 622 transversely to longitudinal axes 613, 631. Rods 612, 630 are coupled to one another in end-to-end fashion with longitudinal axis 613, 631 aligned with one another. Rod 612 includes a rod portion 614, a coupling member 616 having external threads, a contact portion 618 along coupling member 616, and an end member 620. Rod 630 includes a rod portion 632 providing a coupling mechanism 628 having a coupling body 634 integrally formed with rod portion 632. Coupling body 634 includes an axial bore to threadingly receive coupling member 616. Engaging member 642 is threadingly received in trans-axial bore 638 to engage rod 612 at contact surface 618 and prevent it from rotating in coupling body 634.

Figure 15:
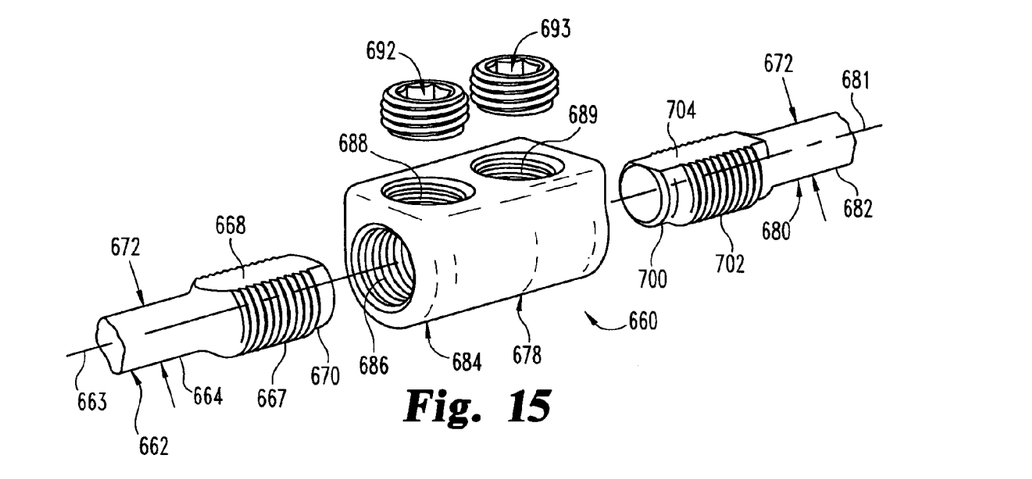
FIG. 15 is an exploded perspective view of a portion of another rod system.
Figure 16:
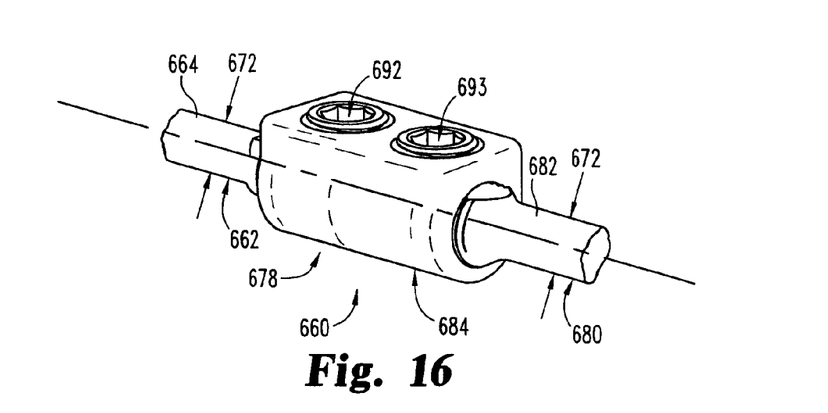
FIG. 16 is an assembled perspective view of the rod system of FIG. 15.

FIGS. 15–16 shown another embodiment rod connection assembly 660 similar to the embodiment shown in FIGS. 9–10, except for rods 662, 680 having the same cross-sectional dimension 672 transversely to longitudinal axes 663, 681. Rods 662, 680 are coupled to one another in end-to-end fashion with longitudinal axis 663, 681 aligned with one another. Rod 662 includes a rod portion 664, a coupling member 667 having external threads, a contact portion 668 along coupling member 667, and an end member 670. Similarly, rod 680 includes a rod portion 682, a coupling member 702 having external threads, a contact portion 704 along coupling member 702, and an end member 700. A coupling mechanism 678 includes coupling body 684 with an axial passage 686 to threadingly engage coupling members 667, 702 in end-to-end fashion with axis 663, 681 aligned with one another. Engaging members 692, 693 are threadingly received in respective ones of trans-axial bores 688, 689 to engage the respective coupling members 667, 702 and prevent rotation of rods 662, 680 in coupling body 684.

Figure 17:
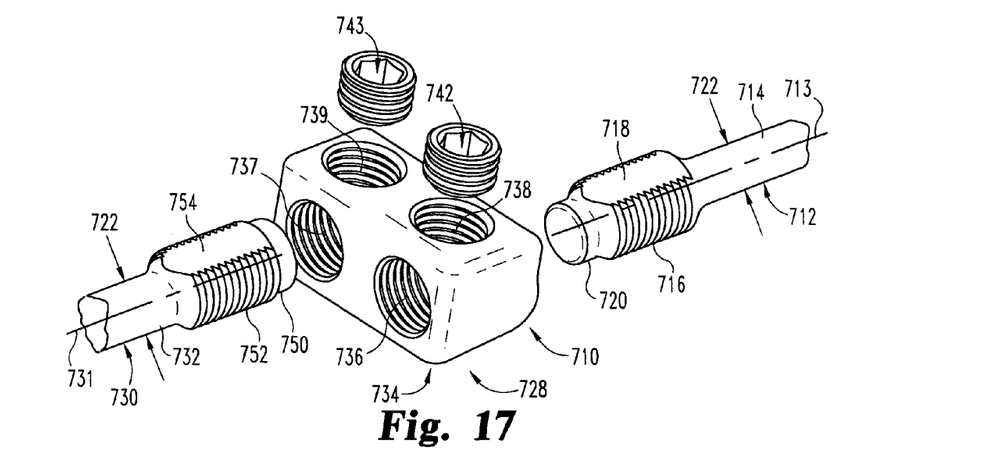
FIG. 17 is an exploded perspective view of a portion of another rod system.
Figure 18:
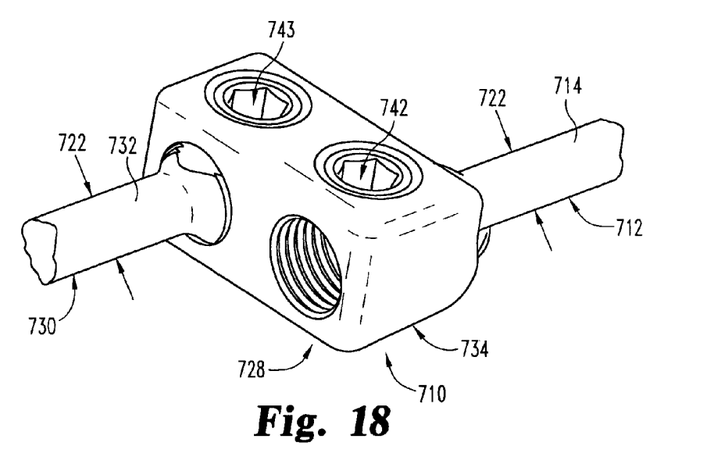
FIG. 18 is an assembled perspective view of the rod system of FIG. 17.

FIGS. 17–18 shown another embodiment rod connection assembly 710 similar to the embodiment shown in FIGS. 11–12, except for rods 712, 730 having the same cross-sectional dimension 722 transversely to longitudinal axes 713, 731. Rods 712, 730 are coupled to one another in end-to-end fashion with longitudinal axis 713, 731 laterally offset from one another. Rod 712 includes a rod portion 714, a coupling member 716 having external threads, a contact portion 718 along coupling member 716, and an end member 720. Similarly, rod 730 includes a rod portion 732, a coupling member 752 having external threads, a contact portion 754 along coupling member 752, and an end member 750. A coupling mechanism 728 includes coupling body 734 with axial passages 736, 737 to threadingly engage coupling members 716, 752 in end-to-end fashion with axes 713, 731 offset laterally relative to one another. Engaging members 742, 743 are threadingly received in respective ones of trans-axial bores 738, 739 to engage the respective coupling members 716, 752 at contact surfaces 718, 754 and prevent rotation of rods 712, 730 in coupling body 734.

While the invention has been illustrated and described in detail in the drawings and foregoing description, the same is to be considered as illustrative and not restrictive in character. All changes and modifications that come within the spirit of the invention are desired to be protected.

What is claimed is:

1. A spinal rod system, comprising:
a first elongated rod extending along a longitudinal axis between a first end and an opposite second end, said first end including a first coupling body having an externally threaded surface profile and a non-threaded first contact surface along at least one side thereof;
a second elongated rod extending along a longitudinal axis between a first end and an opposite second end, said first end including a second coupling body having an externally threaded surface profile and a non-threaded second contact surface along at least one side thereof; and
a coupling mechanism including a coupling member having at least a first bore for threadingly receiving said first and second coupling bodies of said first and second rods in end-to-end fashion with said contact surfaces of said coupling bodies aligned with respective ones of first and second trans-axial bores extending through said coupling member in communication with at least said first bore, said first and second trans-axial bores receiving respective ones of first and second engaging members positionable in contact with respective ones of said first and second contact surfaces to maintain said first and second rods in position relative to said coupling member with said first rod extending in a first direction from said coupling member and said second rod extending in a second direction from said coupling member that is opposite said first direction.

2. The spinal rod system of claim 1, wherein:
said first rod includes a first rod portion with a first characteristic corresponding at least to a first cross-sectional dimension between opposite sides of said first rod portion;
said second rod includes a second rod portion with a second characteristic corresponding at least to a second cross-sectional dimension between opposite sides of said second rod portion; and
said coupling mechanism releasably couples said first and second rods with said opposite sides of each of said first and second rod portions aligned with one another, wherein one of said aligned first and second cross-sectional dimensions is less than the other of said aligned first and second cross-sectional dimensions.

3. The system of claim 2, wherein said coupling member includes a second bore adjacent to and parallel to said first bore, said first bore threadingly receiving said coupling body of said first rod and said second bore threadingly receiving said coupling body of said second rod.

4. The system of claim 3, wherein said first trans-axial bore is in communication with said first bore and said second trans-axial bore is communication with said second bore.

5. The system of claim 4, wherein said first and second trans-axial bores are internally threaded and said first and second engaging members are externally threaded set screws.

6. The system of claim 2, wherein said first and second cross-sectional dimensions correspond to a diameter of respective ones of said first and second rod portions.

7. The system of claim 6, wherein said diameters of said first and second rod portions are the same.

8. The system of claim 6, wherein said diameter of said first rod is less than said diameter of said second rod.

9. The system of claim 1, wherein said contact surfaces are flattened relative to said threaded surface profiles.

10. The system of claim 1, wherein said coupling body is integrally formed with said first rod at said first end of said first rod and said second coupling body is integrally formed with said second rod at said first end of said second rod.

11. The spinal rod system of claim 1, wherein:
said first rod includes a first rod portion extending from said first coupling body along a length to said second end of said first rod, said length sized to extend along a first portion of the spinal column and said first rod portion includes a first characteristic along said length corresponding at least to a first circular cross-section with a first diameter along said length of said first rod portion; and said second rod includes a second rod portion extending along a length from said second coupling body to said second end of said second rod, said length sized to extend along a second portion of the spinal column and said second rod portion includes a second characteristic along said length corresponding at least to a second circular cross-section with a second diameter along said length of said second rod portion, wherein one of said first and second diameters is less than the other of said first and second diameters.

12. A spinal rod system, comprising:

a first elongated rod for attachment to the spinal column, said first rod extending along a longitudinal axis between a first end and an opposite second end, said first rod including a coupling member at said first end and a rod portion extending from said coupling member to said second end with a first characteristic;

a second elongated rod for attachment to the spinal column extending along a longitudinal axis between a first end and an opposite second end, said second rod including a rod portion between said first end and said second end with a second characteristic; and a coupling mechanism including a coupling body extending from said first end of said second rod and including at least a first bore for threadingly engaging and axially constraining said coupling member of said first rod to secure said first and second rods to one another in end-to-end fashion, said coupling mechanism further including an engaging member in said coupling body contactable with said coupling member of said first rod to torsionally constrain said first rod in said coupling body, wherein said first rod portion extends in a first direction from said coupling body and said second rod portion extends in a second direction from said coupling body that is opposite said first direction, wherein said second rod includes a coupling member at said first end thereof and said coupling body threadingly engages said coupling member of said second rod in said first bore opposite said coupling member of said first rod with longitudinal axes of said first and second rods aligned with one another, and wherein said coupling mechanism further includes a second engaging member in said coupling body contactable with said coupling member of said second rod to torsionally constrain said second rod in said coupling body.

13. The system of claim 12, wherein said coupling body includes first and second trans-axial bores extending transversely to and in communication with said first bore, said first and second engaging members including externally threaded set screws threadingly engageable in respective ones of said trans-axial bores.

14. The system of claim 12, wherein the first and second characteristics each include a diameter of a respective one of the first and second rod portions, wherein the first diameter is less than the second diameter.

15. The system of claim 12, wherein the first and second characteristics each include a diameter of a respective one of the first and second rod portions, wherein the first diameter is the same as the second diameter.

16. The system of claim 12, wherein said coupling body is integrally formed with said second rod at said first end of said second rod.

17. The spinal rod system of claim 12, wherein:

said first rod portion of said first rod has a length between said first end and said second end sized to extend along a first portion of the spinal column and includes a first characteristic along said length corresponding at least to a first circular cross-section with a first diameter along said length of said first rod portion;

said second rod portion has a length between said first end and said second end thereof sized to extend along a second portion of the spinal column and includes a second characteristic along said length corresponding at least to a second circular cross-section with a second diameter along said length of said second rod portion, wherein one of said first and second diameters is less than the other of said first and second diameters.

18. The system of claim 12, a spinal rod system, comprising: a first elongated rod for attachment to the spinal column, said first rod extending along a longitudinal axis between a first end and an opposite second end, said first rod including a coupling member at said first end and a rod portion extending from said coupling member to said second end with a first characteristic; a second elongated rod for attachment to the spinal column extending along a longitudinal axis between a first end and an opposite second end, said second rod including a rod portion between said first end and said second end with a second characteristic; and a coupling mechanism including a coupling body extending from said first end of said second rod and including at least a first bore for threadingly engaging and axially constraining said coupling member of said first rod to secure said first and second rods to one another in end-to-end fashion, said coupling mechanism further including an engaging member in said coupling body contactable with said coupling member of said first rod to torsionally constrain said first rod in said coupling body, wherein said first rod portion extends in a first direction from said coupling body and said second rod portion extends in a second direction from said coupling body that is opposite said first direction, and wherein said second rod includes a coupling member at said first end thereof and said coupling body includes a second bore adjacent and parallel to said first bore for threadingly receiving said coupling member of said second rod with longitudinal axes of said first and second rods laterally offset from one another.

19. The system of claim 18, wherein said coupling body includes first and second trans-axial bores extending transversely to and in communication with respective ones of said first and second bores, said first engaging member being received in said first trans-axial bore and a second engaging member being received in said second trans-axial bore to torsionally constrain said second rod in said coupling body.

20. A method for assembling a spinal rod system, comprising:

providing a first spinal rod with a first rod portion for attachment along the spinal column, said first rod portion including a first characteristic and a coupling member at an end of the rod portion extending along an axis of the first spinal rod;

providing a second spinal rod with a second rod portion for attachment along of the spinal column, said second rod portion including a second characteristic;

threadingly engaging the coupling member of the first spinal rod to a coupling body extending between the first spinal rod and the second spinal rod;

threadingly engaging an engaging member to the coupling body and positioning the engaging member in contact with the coupling member of the first spinal rod to torsionally constrain the first spinal rod in the coupling body with the first spinal rod and the second spinal rod in end-to-end arrangement relative to one another and extending in opposite directions from one another from the coupling body;

threadingly engaging a coupling member at said first end of said second spinal rod to said coupling body; and threadingly engaging a second engaging member to the coupling body in contact with the coupling member of the second spinal rod to torsionally constrain the second spinal rod in the coupling body.

21. The method of claim 20, wherein in the end-to-end arrangement longitudinal axes of the first and second spinal rods are aligned with one another.

22. The method of claim 19, wherein in the end-to-end arrangement longitudinal axes of the first and second spinal rods are laterally offset from one another.

23. The method of claim 20, wherein providing the first spinal rod includes providing the first rod portion with a circular cross-section with a first diameter along an entire length thereof and providing the second spinal rod includes providing the second rod portion with a circular cross-section with a second diameter along an entire length thereof, wherein one of the first and second diameters is less than the other of the first and second diameters.

* * * * *